United States Patent
Mosler et al.

(10) Patent No.: US 7,632,256 B2
(45) Date of Patent: Dec. 15, 2009

(54) CATHETER GRIPPING DEVICE

(76) Inventors: Theodore J. Mosler, 5433 Alafia Ct., Raleigh, NC (US) 27616; Todd M. Korogi, 8701 Walkelin Ct., Raleigh, NC (US) 27615; Scott P. Jarnagin, 433 Guilford Cir., Raleigh, NC (US) 27608; John H. Golden, 1312 Ponce de Leon Ave., Atlanta, GA (US) 30306

(*) Notice: Subject to any disclaimer, the term of this patent is extended or adjusted under 35 U.S.C. 154(b) by 16 days.

(21) Appl. No.: 11/552,316

(22) Filed: Oct. 24, 2006

(65) Prior Publication Data

US 2008/0097362 A1    Apr. 24, 2008

(51) Int. Cl.
| | |
|---|---|
| A61F 5/44 | (2006.01) |
| A61M 5/32 | (2006.01) |
| A61M 5/00 | (2006.01) |
| A61M 31/00 | (2006.01) |
| A61M 25/00 | (2006.01) |
| A61M 1/00 | (2006.01) |
| A61M 27/00 | (2006.01) |
| A61F 11/00 | (2006.01) |
| A61B 17/00 | (2006.01) |
| A61B 17/50 | (2006.01) |

(52) U.S. Cl. .................. 604/349; 604/177; 604/262; 604/263; 604/273; 604/275; 604/523; 604/540; 604/544; 606/108; 606/205; 606/211

(58) Field of Classification Search .............. 604/317, 604/327, 328, 349, 351, 540, 541, 543, 544, 604/177; 606/1
See application file for complete search history.

(56) References Cited

U.S. PATENT DOCUMENTS

| | | | | |
|---|---|---|---|---|
| 3,556,294 A | * | 1/1971 | Walck et al. .............. 206/210 |
| 3,766,915 A | * | 10/1973 | Rychlik .................... 604/161 |
| 3,854,483 A | | 12/1974 | Powers ..................... 128/349 |
| 4,062,363 A | | 12/1977 | Bonner, Jr. ................ 128/349 |
| 4,673,161 A | * | 6/1987 | Flynn et al. .................. 251/10 |
| 4,985,018 A | * | 1/1991 | Smith ....................... 604/161 |
| 5,120,320 A | * | 6/1992 | Fayngold ................... 604/177 |
| 5,147,341 A | | 9/1992 | Starke et al. ............... 604/349 |
| 5,188,612 A | * | 2/1993 | Herrington et al. ......... 604/192 |
| 5,226,530 A | | 7/1993 | Golden .................... 206/210 |
| 5,226,892 A | * | 7/1993 | Boswell .................... 604/180 |
| 5,368,575 A | * | 11/1994 | Chang ...................... 604/174 |
| 5,454,798 A | * | 10/1995 | Kubalak et al. ............ 604/328 |
| 6,004,305 A | | 12/1999 | Hursman et al. ........... 604/328 |

(Continued)

OTHER PUBLICATIONS

The Cathgrip, BioDerm, http://www.bioderm.us/index.php?option=com_content&view=article&id=64&Itemid=148.

*Primary Examiner*—Leslie R Deak
*Assistant Examiner*—Adam Marcetich
(74) *Attorney, Agent, or Firm*—FSB Legal Counsel, LLP

(57) ABSTRACT

The present invention relates to a urinary catheter gripping device for use with a urinary catheter located within a urinary catheter pouch. In one aspect, the urinary catheter pouch has a port defined in its exterior surface, whereby the port is in communication with the interior cavity of the urinary catheter pouch. In this aspect, the urinary catheter is substantially disposed therein the pouch and is configured to selectively pass therethrough the port. The gripping device can be positioned on the pouch at any convenient location that aids in the holding of the catheter.

18 Claims, 13 Drawing Sheets

U.S. PATENT DOCUMENTS

| | | | |
|---|---|---|---|
| 6,053,905 A | 4/2000 | Daignault, Jr. et al. | 604/544 |
| 6,235,006 B1* | 5/2001 | Dillon et al. | 604/263 |
| 6,497,681 B1* | 12/2002 | Brenner | 604/164.05 |
| 6,578,709 B1* | 6/2003 | Kavanagh et al. | 206/364 |
| 6,602,224 B1 | 8/2003 | Simhambhatla | 604/96.01 |
| 7,014,627 B2* | 3/2006 | Bierman | 604/174 |
| 7,175,610 B2* | 2/2007 | Mori | 604/263 |
| 2002/0103467 A1* | 8/2002 | Kubalak | 604/327 |
| 2002/0133130 A1* | 9/2002 | Wilcox | 604/349 |
| 2003/0130646 A1* | 7/2003 | Kubalak et al. | 604/544 |
| 2004/0147880 A1* | 7/2004 | Duffy et al. | 604/263 |
| 2005/0015076 A1* | 1/2005 | Giebmeyer et al. | 604/544 |
| 2007/0161971 A1* | 7/2007 | House | 604/544 |

* cited by examiner

CATHETER GRIPPING DEVICE

BACKGROUND OF THE INVENTION

1. Field of the invention

The present invention relates to a gripping device for gripping a urinary catheter within a closed pouch. Particularly, the invention relates to a device that allows the user of a urinary catheter contained within a sterile urinary catheter pouch to manually grip the urinary catheter as it is advanced out of the pouch for use, with minimal need for user dexterity or personal grip strength.

2. Background of the Invention

A wide variety of catheters are available for insertion into the body for introduction or withdrawal of fluids. Urinary catheters are flexible tubes designed to drain urine from the bladder by insertion into the urethra. They are packaged in sterile containers and can be lubricated for insertion prior to packaging or prior to use. Intermittent urinary catheters are designed to be inserted for each use and are commonly used by patients who are able to catheterize themselves. One type of intermittent catheter comprises a urine catheter pouch, which also serves as the sterile package for the catheter. See, for example, U.S. Pat. No. 3,854,483 to Powers, U.S. Pat. No. 5,226,530 to Golden, U.S. Pat. No. 6,004,305 to Hursman et al, U.S. Pat. No. 5,147,341 to Starke et al and U.S. Pat. No. 6,053,905 to Daignault et al. Another type of catheter is an intermittent catheter contained in a conduit pouch, whereby the pouch can be opened and used to transfer urine to the toilet or a urine collection container.

Catheterization is accomplished by introducing the proximal tip of a catheter into the urethra, and then "longitudinally collapsing and extending the pouch in an accordion-like manner until the tip reaches the bladder" as described in U.S. Pat. No. 6,602,224 to Kavanagh and U.S. Pat. No. 4,062,363 to Bonner. The portion of the catheter remaining within the pouch is gripped between the walls of the pouch advanced out of the pouch and into the urethra. During the pouch-extending phase, the catheter is held to resist a movement of the catheter back into the pouch by gripping the catheter between the pouch walls. The operation requires two hands to accomplish, as well as dexterity to make sure that the catheter does not retract back into the pouch. It is a difficult, if not impossible, activity for a quadriplegic, high paraplegic or person with low grip strength to accomplish. Few, if any, products serve the self catheterization market for these users.

Further, complications can make the process next to impossible, even for those with great dexterity or strength. For example, the fluid pressure from the bladder or the weight from the urine may tend to pull the lubricated catheter from the urethra and back into the urinary catheter pouch. To prevent this from occurring, the user must continuously grip the catheter until voiding is completed. Catheters are normally heavily lubricated and have to be gripped between the walls of the plastic pouch. This can create a "slippery noodle" effect, which means that the grip strength and dexterity required to immobilize the catheter from retracting into the pouch may be so great that self-catheterization becomes impossible, even for someone with normal grip strength.

What is needed is a device to assist in the gripping of a urinary catheter, while it is in a urinary catheter pouch, for use by persons with limited strength and dexterity.

SUMMARY OF THE INVENTION

The present invention relates to a urinary catheter gripping device for use with a urinary catheter located within a urinary catheter pouch. In one aspect, the urinary catheter pouch has a port defined in its exterior surface, whereby the port is in communication with the interior cavity of the urinary catheter pouch. In this aspect, the urinary catheter is substantially disposed therein the pouch and is configured to selectively pass therethrough the port. The gripping device can be positioned on the pouch at any convenient location that aids in the holding of the catheter.

The gripping device, in one aspect, comprises a gripper assembly with a first gripper member and a second gripper member. In one aspect, the first and second gripper members define the catheter pathway to be configured such that a catheter may fit in the pathway, along with the pouch material, when the catheter is gripped through the pouch walls with the gripping device. The pathway is further designed to allow the catheter to move therethrough when the gripping device is being repositioned with respect to the catheter as the gripping device is disengaged.

These and other objects of the present invention will be clear when taken in view of the detailed specification and disclosure in conjunction with the appended figures.

DETAILED DESCRIPTION OF THE DRAWINGS

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

Figure 1:
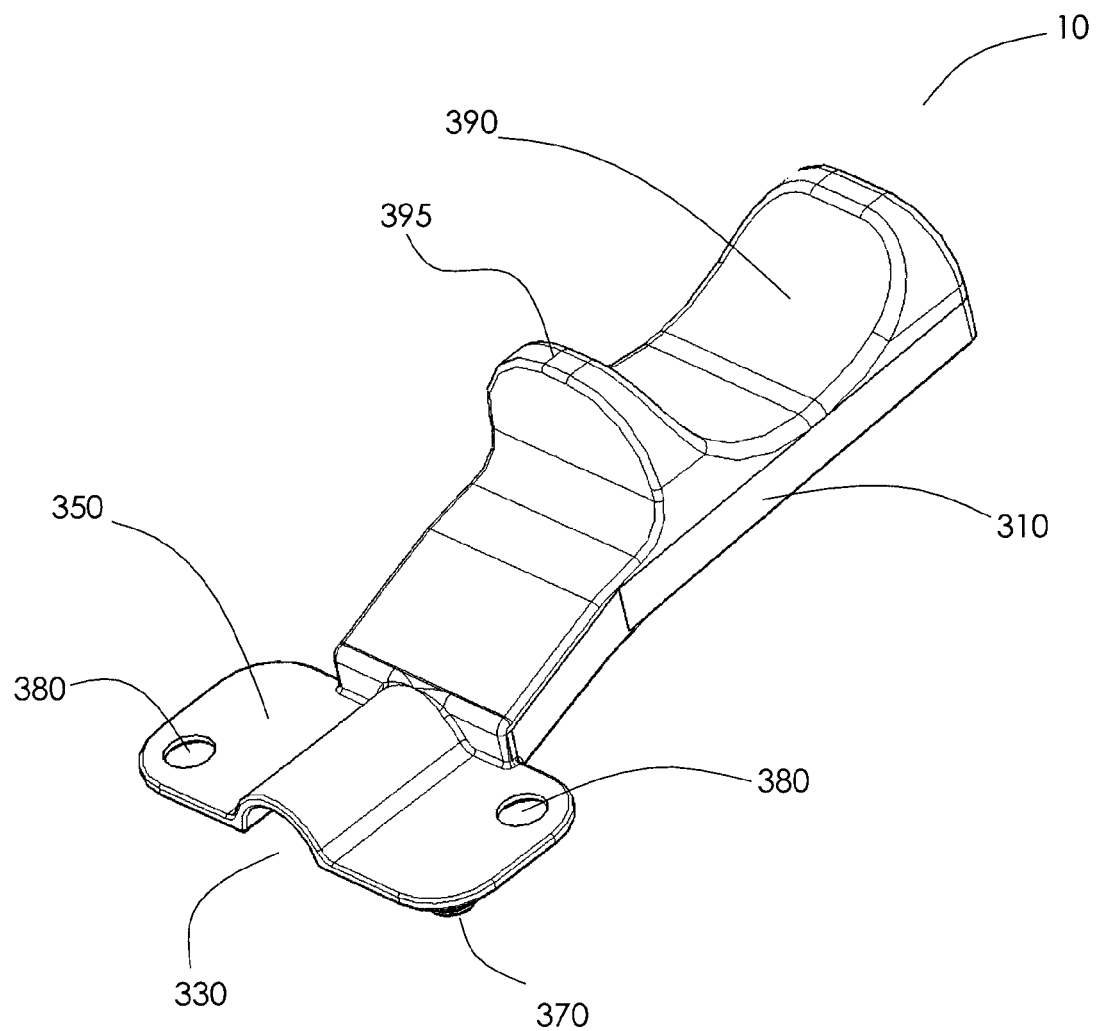
FIG. 1 is a top perspective view of one gripper member of the gripping device according to the present invention.
Figure 2:
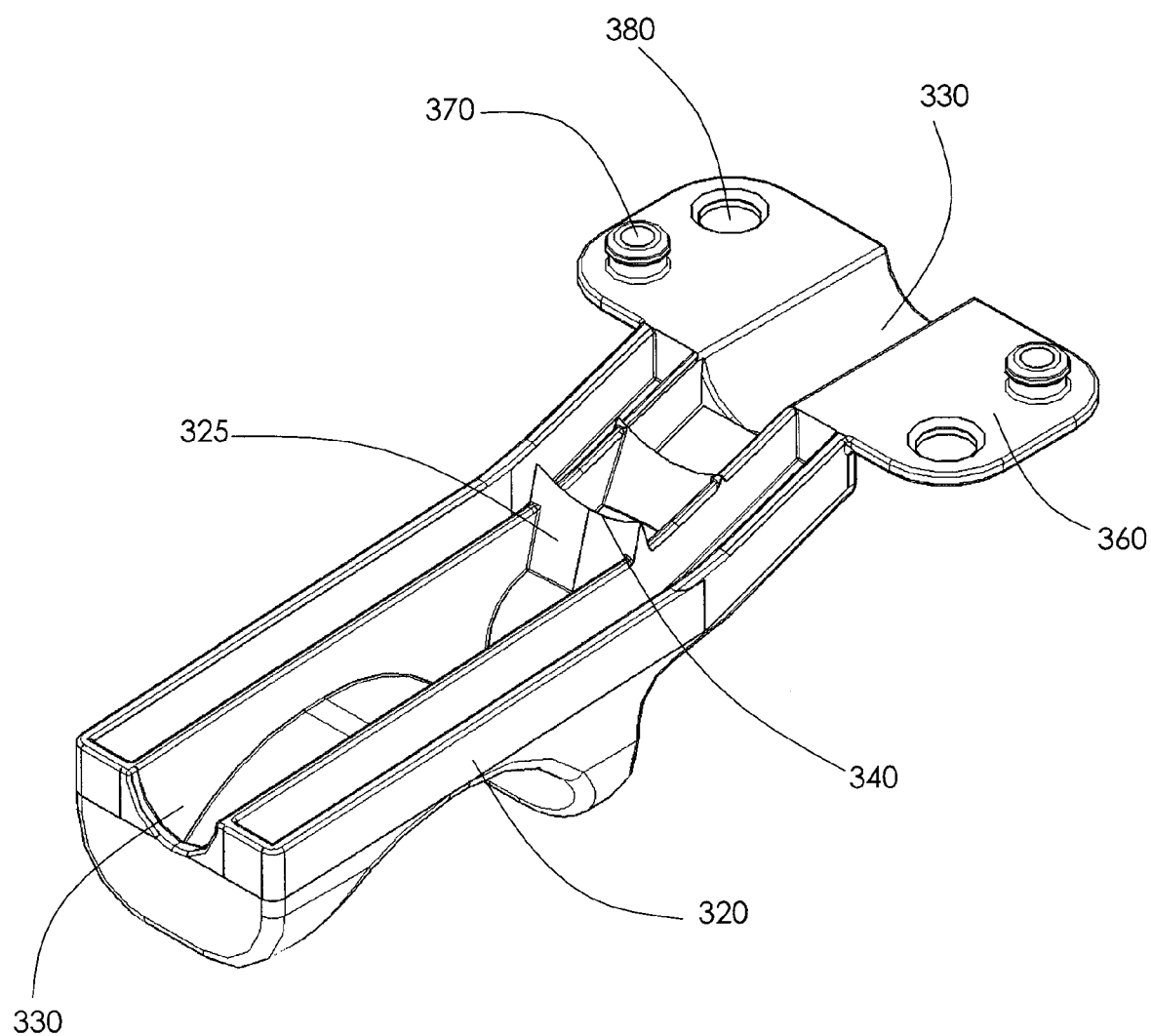
FIG. 2 is a bottom perspective view of one gripper member of the gripping device of FIG. 1.
Figure 3:
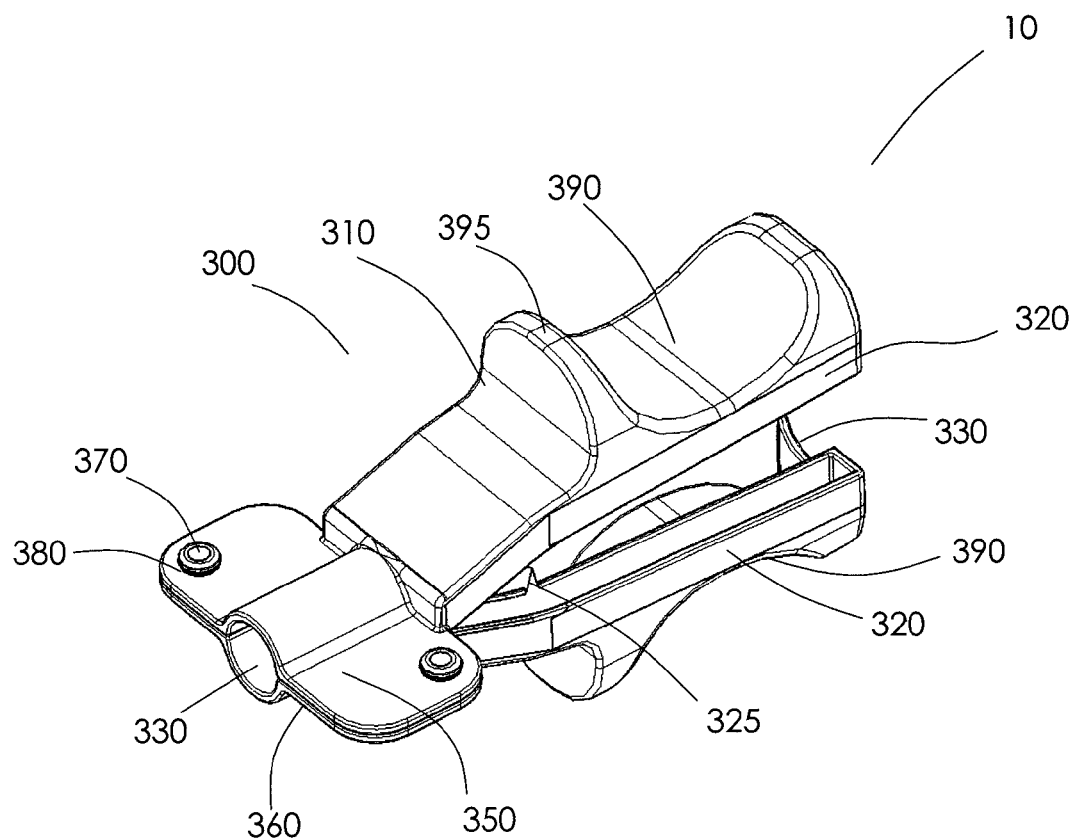

FIG. 3 a top perspective view of the gripping device of FIG. 1.

Figure 4:
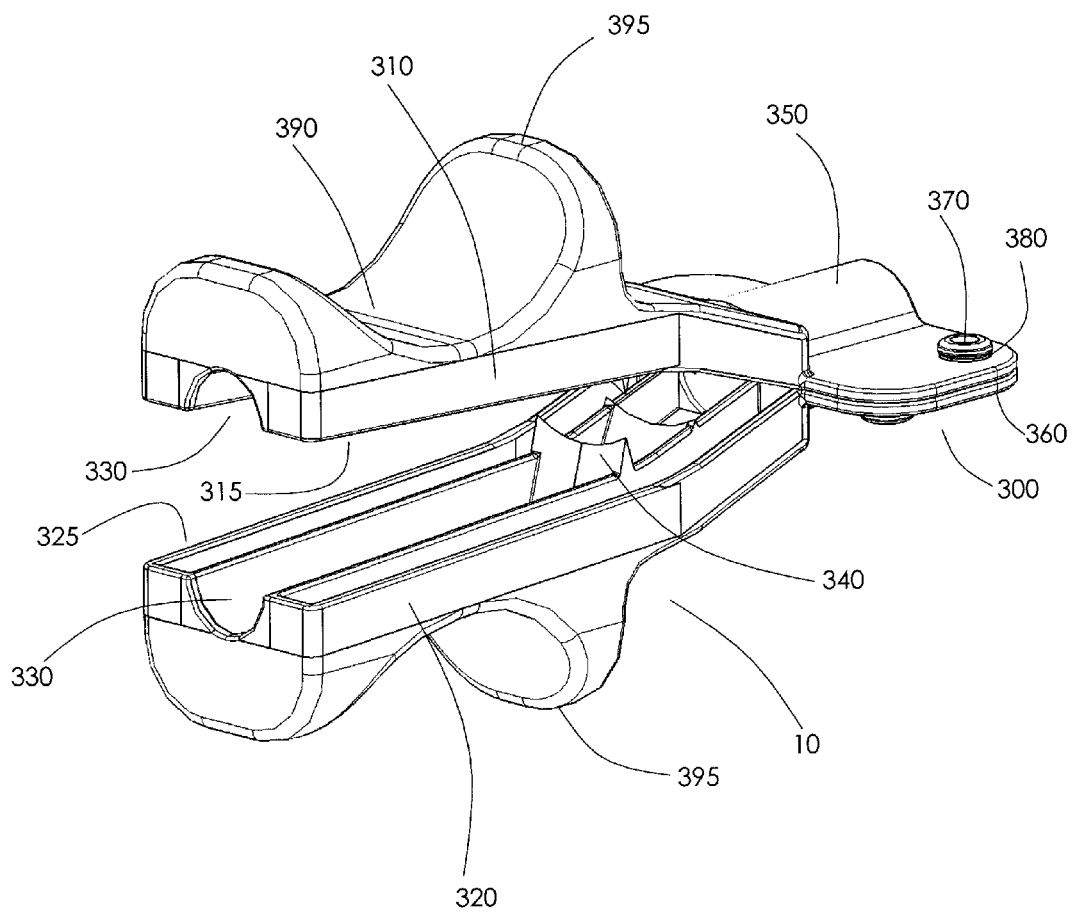

FIG. 4 is a side perspective view of the gripping device of FIG. 1.

Figure 5:
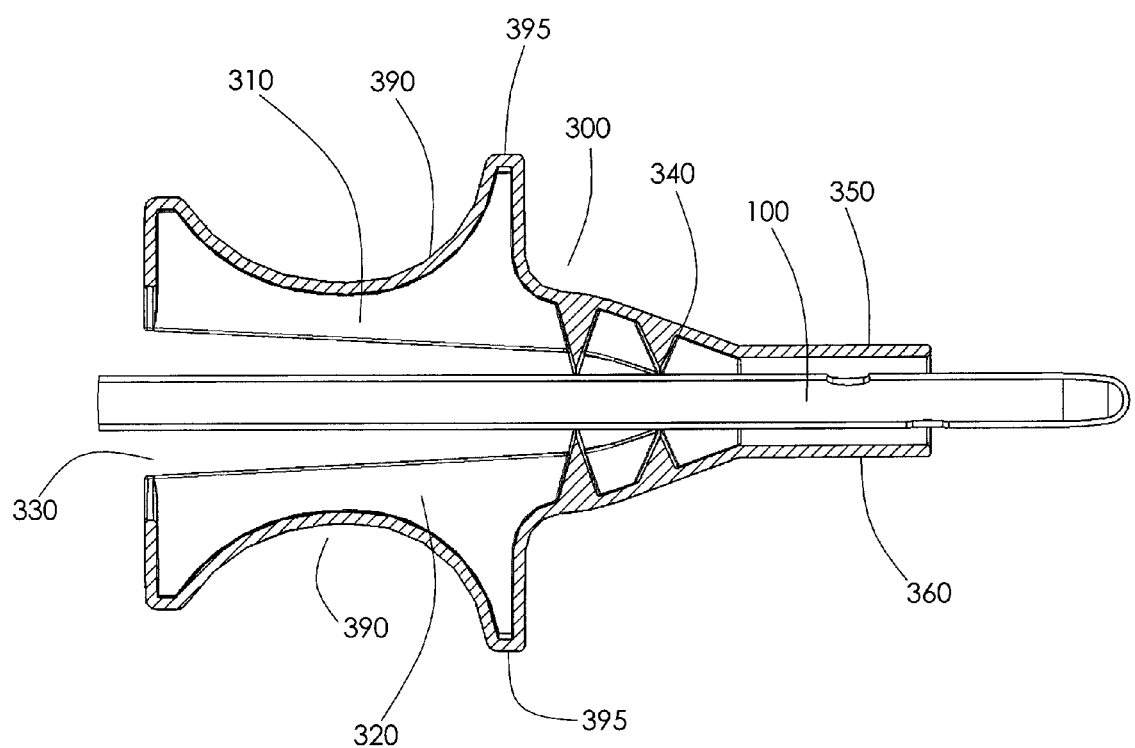

FIG. 5 is a cross-sectional view of the gripping device of FIG. 1, showing a urinary catheter within a urinary catheter pathway.

Figure 6:
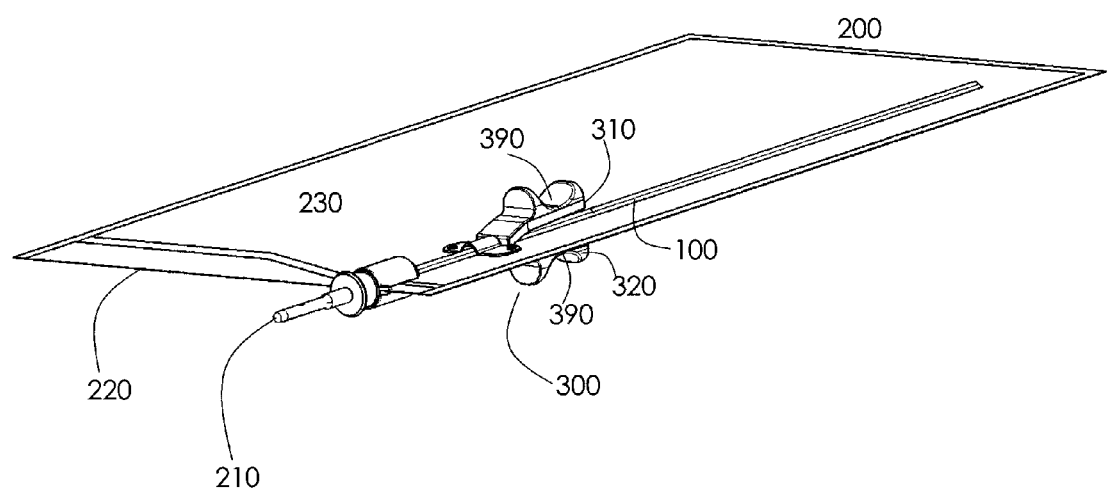

FIG. 6 is a perspective view of the gripping device of FIG. 1, mounted on a urinary catheter pouch.

Figure 7:
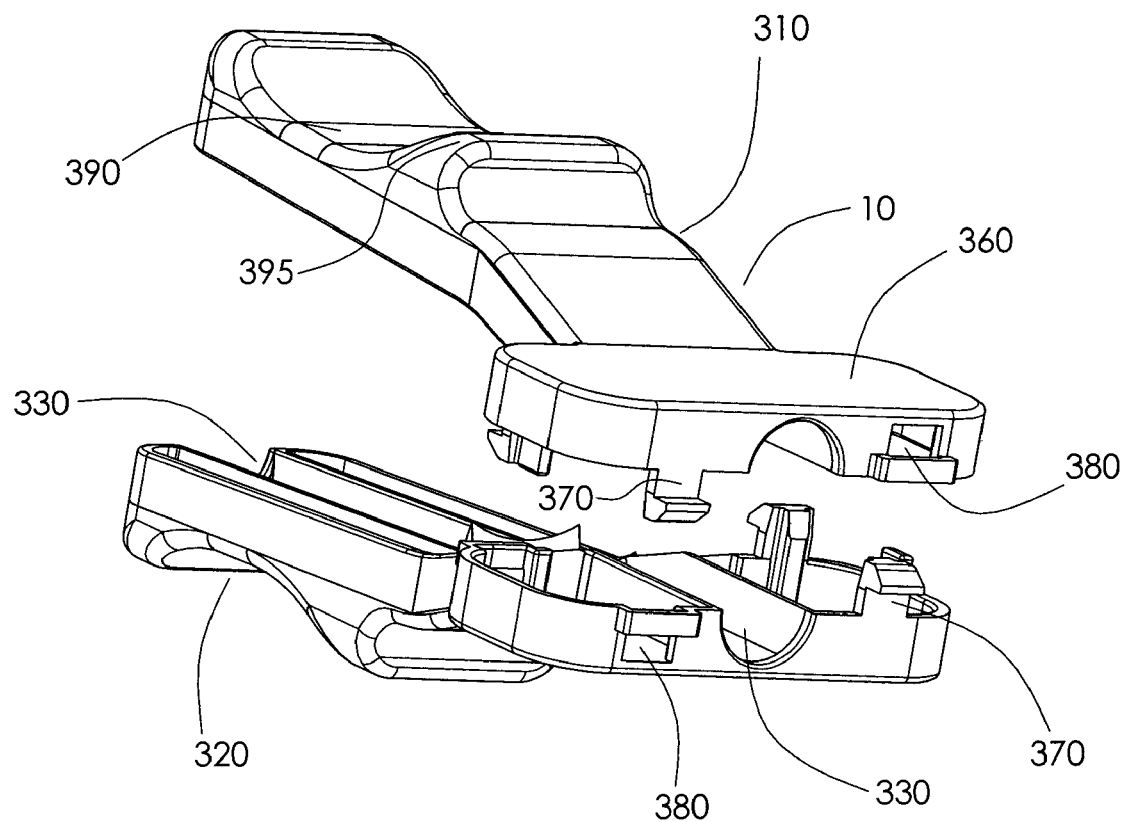

FIG. 7 is a perspective view of an alternate embodiment of the gripping device according to the present invention.

Figure 8:
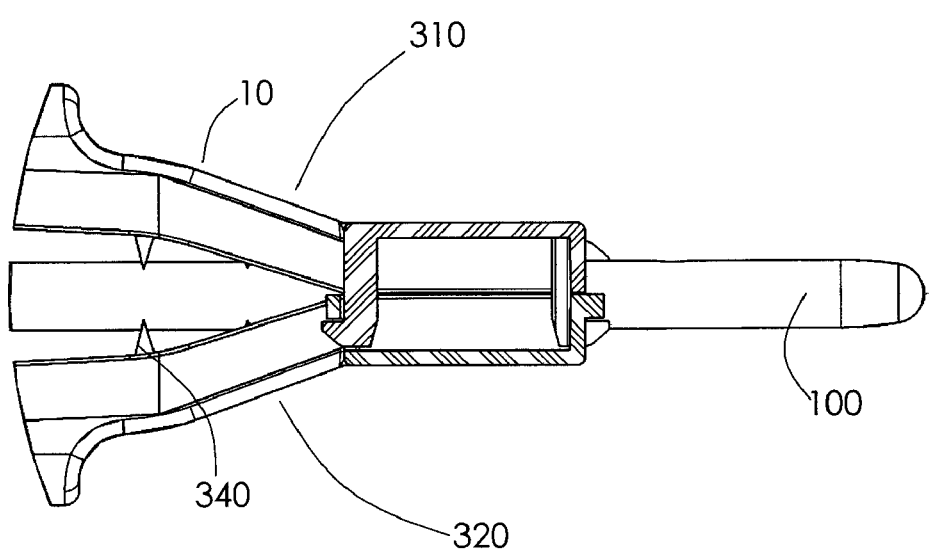

FIG. 8 is a cross-sectional view of the gripping device of FIG. 7, showing two pincher points.

Figure 9:
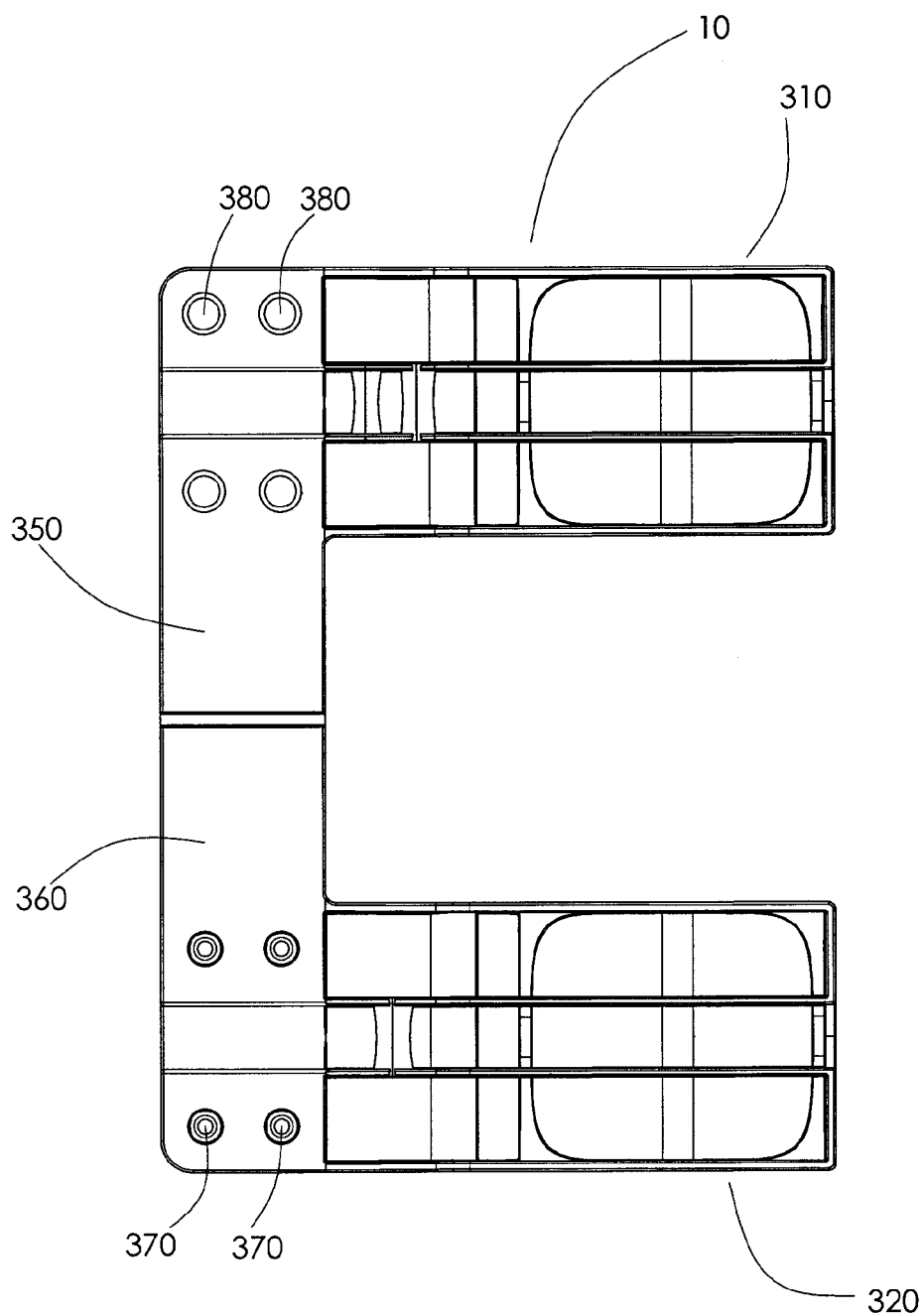

FIG. 9 is an opened assembly view of an alternate embodiment of the gripping device according to the present invention, where the first and second gripper members are permanently joined.

Figure 10:
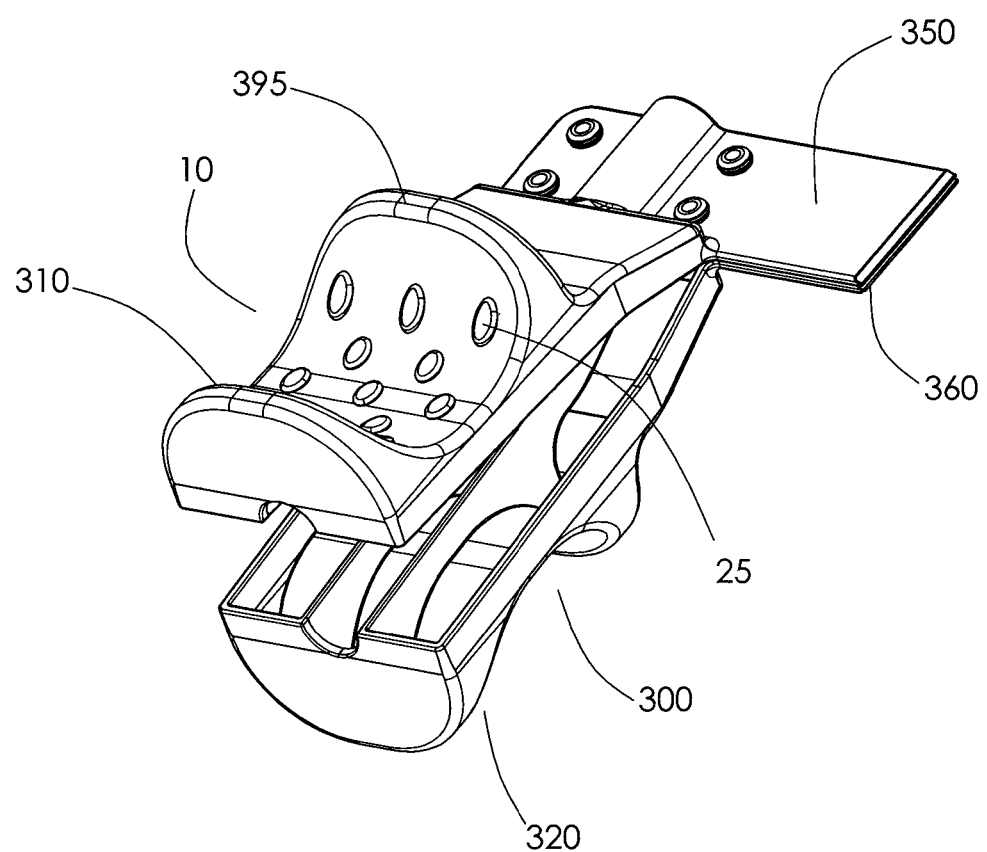

FIG. 10 is a perspective view of the gripping device of FIG. 9.

Figure 11:
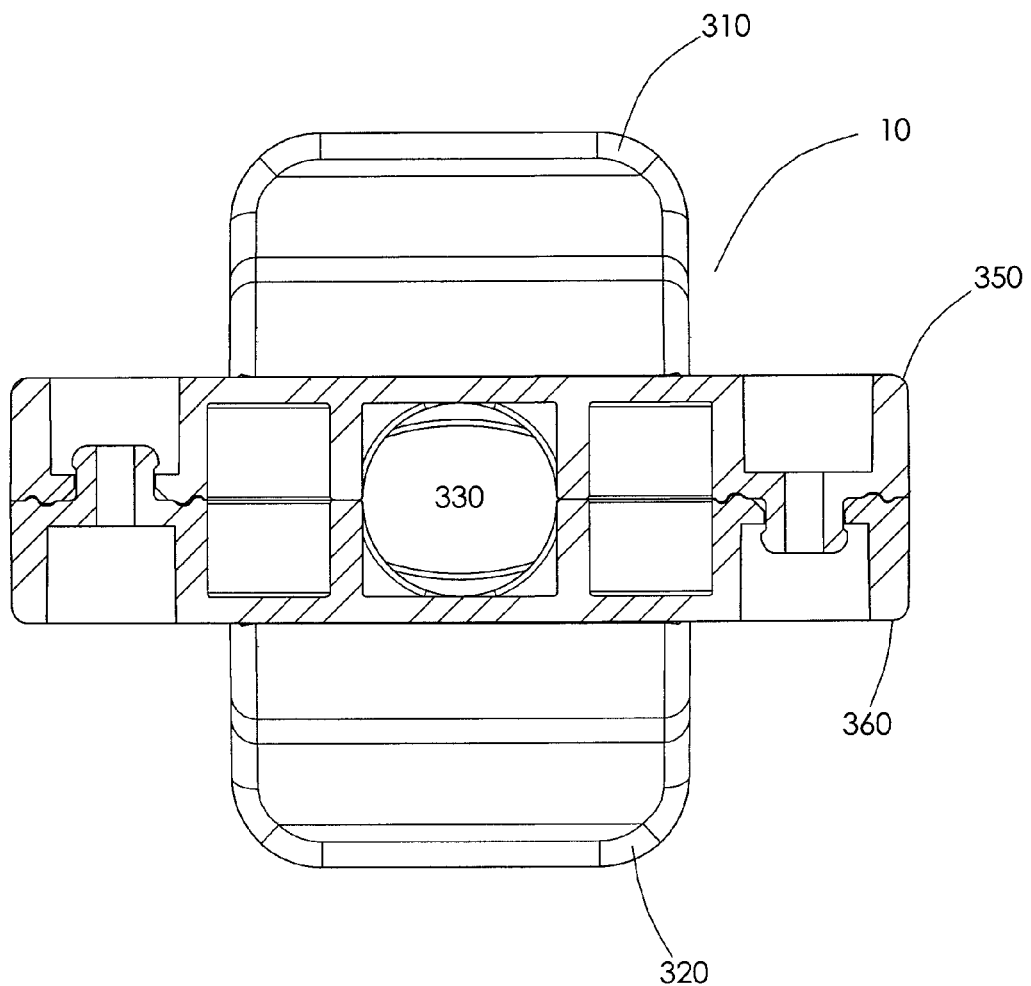

FIG. 11 is a frontal view of the gripping device of FIG. 7, showing gripper seals.

Figure 12:
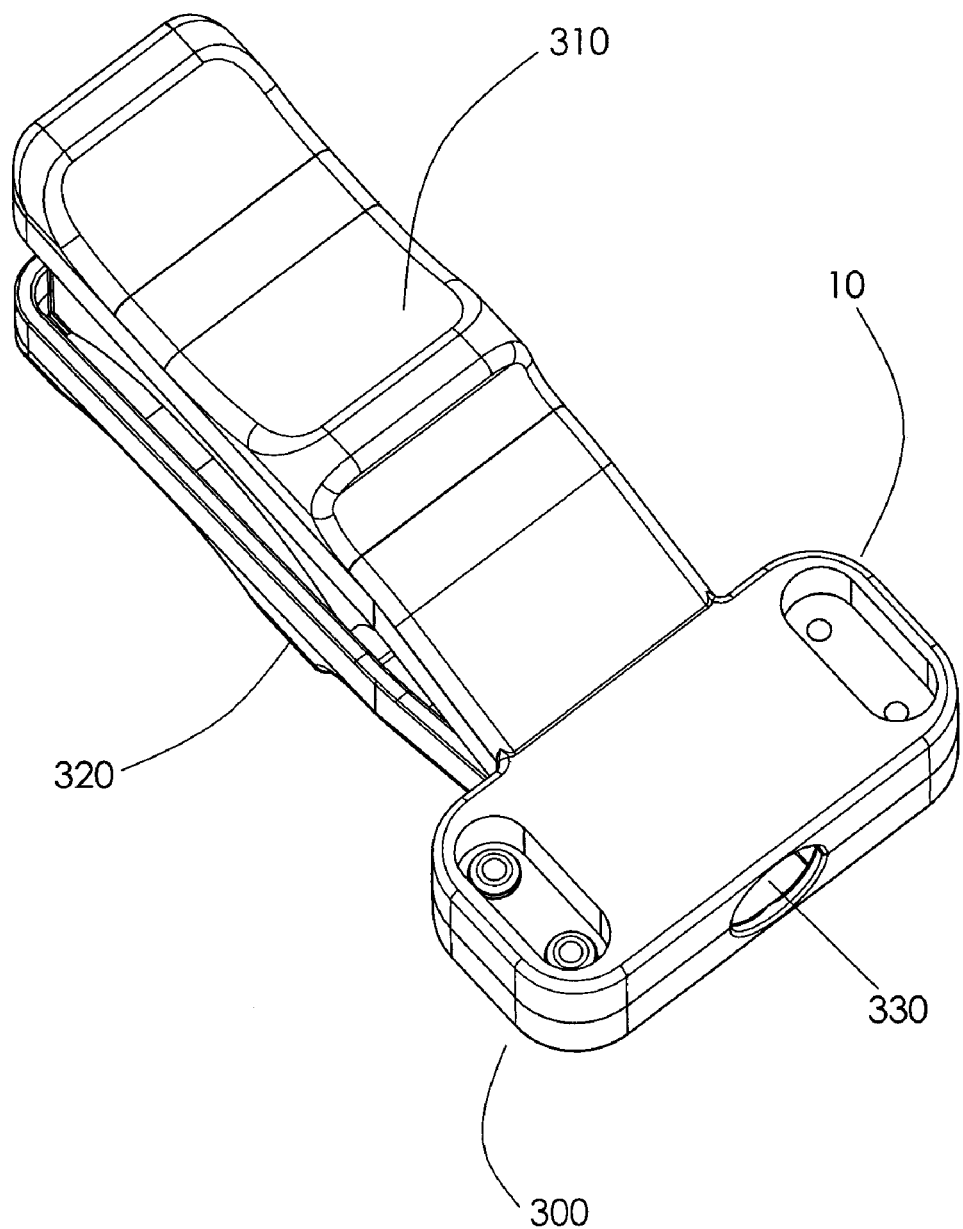

FIG. 12 is a perspective view of the gripping device of FIG. 11.

Figure 13:
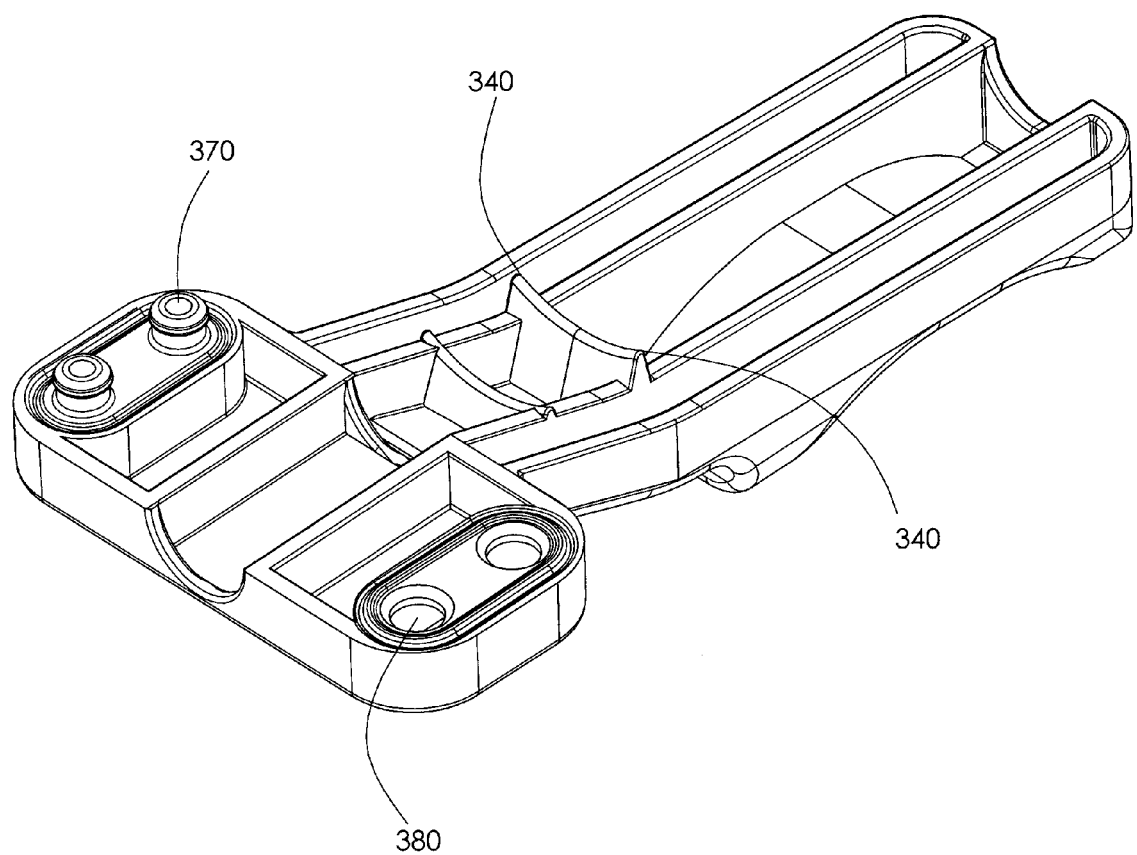

FIG. 13 is a perspective view of on gripper members of the gripping device of FIG. 7, showing the gripper seals and a pincher point.

DETAILED DESCRIPTION OF THE INVENTION

The present invention may be understood more readily by reference to the following detailed description of the invention and the Examples included therein and to the Figures and their previous and following description.

Before the present systems, articles, devices, and/or methods are disclosed and described, it is to be understood that this invention is not limited to specific systems, specific devices, or to particular methodology, as such may, of course, vary. It is also to be understood that the terminology used herein is for the purpose of describing particular embodiments only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used in the specification and the appended claims, the singular forms "a," "an" and "the" include plural referents unless the context clearly dictates otherwise. Thus, for example, reference to "a gripping device" includes two or more such gripping devices, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

The present invention relates to a urinary catheter gripping device 10 for use with a urinary catheter 100 located within a urinary catheter pouch 200. In one aspect, the urinary catheter pouch 200 has a port 210 defined in its exterior surface 220, whereby the port 210 is in communication with the interior cavity 230 of the urinary catheter pouch. In this aspect, the urinary catheter 100 is substantially disposed therein the pouch and is configured to selectively pass therethrough the port. As one skilled in the art can appreciate, the catheter may or may not be lubricated.

The gripping device 10 can be positioned on the pouch at any convenient location that aids in the holding of the catheter. In one embodiment, the user or health care worker obtains the gripping device separately from the catheter and positions and attaches the gripping device in a desired location on the urine catheter pouch for optimum use of the individual user. In other embodiments, the gripping device is pre-positioned and attached prior to use by the end user or health care worker. Normally, a location closer to the user would be preferred, but positioning is well within the skill in the art.

The gripping device 10, in one aspect, comprises a gripper assembly 300 with a first gripper member 310 and a second gripper member 320. In another aspect, the first gripper member 310 comprises a first pinch face 315 and the second gripper member 320 comprises a second pinch face 325. The first and second gripper members may be attached to each other such that they define a catheter pathway 330. In one aspect, the first and second gripper members define the catheter pathway 330 to be configured such that a catheter 100 may fit in the pathway, along with the pouch material, when the catheter is gripped through the pouch walls with the gripping device The pathway is further designed to allow the catheter to move therethrough when the gripping device is being repositioned with respect to the catheter as the gripping device is disengaged. In one aspect, the pathway extends from the point of attachment of the gripping device to the opposite end of the gripping device 10. In another aspect, the pathway is essentially half of a channel on the pinch face side of each gripper member. The shape of the pathway can be tubular, rectangular, or a combination of shapes. However, regardless of the exact shape, it will define a bounded area that the catheter can move through. In one aspect, the catheter pathway 330 is tubular at each end and is a bounded area in the middle which is in the shape of the pinch face side of the gripper member.

Each gripper member may act as a lever arm. "Lever arm," as meant herein, is a rigid or semi-rigid bar or beam that is free to pivot, bend, flex or the like around a fixed point or moment in order to take advantage of the mechanical force produced by the moment action. The two gripper members of the invention may be positioned in opposing positions to produce an opposing gripping force from both sides of a catheter 100 to be gripped. When applying force to each gripper member in combination, the gripping device increases the amount of force being applied to the catheter, as compared with gripping the catheter directly through the urinary catheter pouch with fingers alone. Each gripper member can be, for example, made of a substantially rigid or semi-rigid material, such as a rigid polymer, metal, wood, laminated material, or the like. Some examples of suitable rigid polymers of the invention include polypropylene, polyethylene, polycarbonate, or the like. Further, rigidity or flexibility can be adjusted by the thickness of the material selected, design factors, such as cross beams, as well as other structural support means known in the art.

In yet another aspect, the gripper assembly 300 is configured to attach to the exterior surface 220 of the urinary catheter pouch, such that the catheter, which is located within the interior cavity 230 of the urinary catheter pouch, is positioned substantially within the catheter pathway. As such, in one aspect, at least a portion of at least one of the first and second gripper members are selectively movable between a first position, in which the respective first and second pinch faces of the first and second gripper members do not engage the urinary catheter (the catheter is free to move relative to the catheter pathway), and a second position, in which at least a portion of the respective first and second pinch faces of the first and second gripper members engage a portion of the urinary catheter such that the catheter is prevented from moving relative to the catheter pathway. In use, the user engages the gripping device to the catheter 100, advances a portion of the catheter therethrough a port in the urinary catheter pouch, disengages the gripping device from the catheter, repositions the gripper to another point along the longitudinal length of the catheter, and repeats the process until a sufficient length of the catheter has been advanced to achieve urine flow.

In one aspect of the invention for a urinary catheter gripping device, the first pinch face 315 of the first gripper member is positioned adjacent the second pinch face 325 of the second gripper member 320. In another aspect, the first pinch face of the first gripper member substantially faces the second pinch face of the second gripper member. In this aspect, the second pinch face of the second gripper member is configured to cooperate with the first pinch face of the first gripper member 310.

In one aspect, each pinch face comprises one or more pincher points 340. For example, and not meant to be limiting, the pincher points 340 may comprise a plurality of protrusions configured to grasp the urinary catheter 100 within the catheter pathway 330. In this aspect, when force is applied to each gripper member, most of the force is directed to the pincher points. By "pincher points" it is meant herein as a means for grasping, crimping or otherwise immobilizing or preventing longitudinal movement of a catheter positioned in the catheter pathway when the gripping device is engaged. In one aspect, the pincher points are designed such that they will not puncture the urinary catheter pouch 200 nor damage the catheter during use. In another aspect, the pincher points consist of one or more protrusions of a shape designed to function as described. One embodiment is a triangular shaped pincher point, although a rectangular or other type pincher point is also disclosed. Likewise, the choice of one, two, or more pincher points 340 will depend on the size of the catheter, the material from which it is made, as well as a number of other physical factors known in the art. The pincher points can be on one gripper member or both gripper members. For ease in manufacturing, identical gripper members can be manufactured as suggested above, thus having opposing pincher points on opposite sides of a catheter placed in the channel. In another embodiment, the pincher points are staggered.

The length of each gripper member depends on several factors. In one aspect, each gripper member is the same length. As one skilled in the art will appreciate, the longer the lever, the greater the grip strength created. However, the longer the gripper members are, the further the arms stick out from the urinary catheter pouch surface when used, thus creating an obstruction. If grip strength is too great, the pincher points 340 can damage the urinary catheter pouch 200 or the catheter 100 during use. The length of the gripper member will depend on the size of the catheter as well. One skilled in the art in view of this disclosure can vary the length of the gripper member and optimize the length for a given catheter and urinary catheter pouch combination. In one aspect, the length of the lever is from about 1.25 cm to about 15 cm. In another aspect, the gripper member is straight. However, in yet another aspect, the gripper member has an angle bend from about 20 degrees to about 60 degrees.

In one aspect, the gripper members are positioned such that, in their open relaxed state, they do not impede the movement of the catheter in the catheter pathway. Particularly, the pincher points should allow for the movement of the catheter during distal or proximal movement. One way to achieve this, for example, is to ensure the levers are about 25-45 degrees relative to the surface of the pouch 200 to achieve catheter clearance.

In yet another aspect of the invention, the first gripper member comprises a first mount member 350 that is hingedly connected to the first pinch face 315. In one aspect, the second gripper member 320 also comprises a second mount member 360 that is connected to the second pinch face 325. The second mount member 360 may be hingedly connected to the second pinch face. The mount members are configured to engage an outer portion of the urinary catheter pouch to mount the gripping device 10 thereto.

The mount members, as discussed herein, have a variety of means for attaching the gripping device to the urinary catheter pouch. For instance, at least one male tab 370 may extend therefrom at least one of the respective first and second mount members. The male tab 370 would be configured to be operatively received within at least one female cavity 380 which would be defined therein at least one of the respective first and second mount members. In one aspect, each male tab and each female cavity 380 form a snap-fit connection. In another aspect, as the mount members are attached to a portion of the urinary catheter pouch, the exterior surface of the urinary catheter pouch is interposed therebetween the connected first and second mount members such that first mount member is connected to the front face of the urinary catheter pouch and the second mount member 360 is connected to the back face of the urinary catheter pouch 200. This "snap-fit" method is easy to attach, but takes a great deal of force to disengage. In one aspect, there are 2 or more corresponding male tabs and female cavities. In yet another aspect, the female cavities and male tabs are matching such that identical gripper members can be used for the first and second gripper members of the invention and when lined up on opposite sides of the pouch their opposing male tabs 370 and female cavities align. In another aspect, the mount members are attached to the pouch by use of cantilever beam tabs and cavities, as seen in FIG. 7. The male tabs can also be designed to puncture the bag. Where snaps, rivets, or the like are used, which puncture the pouch, a pin or the like that is used can be swaged or heat staked to increase locking force.

Where the bag is punctured by the attachment mechanism, various means to seal the puncture from leakage can be used. For example, sealing washers or O-rings can be used to prevent leakage.

Each of the gripper members may also comprise a gripping tab 390. A "gripping tab" as used herein is a surface texture treatment of the gripping device that allows a more secure place to grip with the fingers by increasing the friction or surface area of the surface in the area to be gripped. This can be accomplished by roughing the area, placing knobs, raised surface bumps, or the like, which increase surface area and make gripping by the fingers easier. It can also be an indentation, a valley, or a flat area that holds the fingers relatively stationary at the desired location. The gripping tab 390 can be constructed as either a universal hand style, or be angled to be used by either a right hand or left hand. It could also be designed to be gripped by the thumb and forefinger or the crook of the hand between the thumb and forefinger. The area to be gripped can be positioned toward the distal end of each gripper member in order to make the most use of the leverage produced by the gripper member.

In one aspect, the first gripper member is equipped with a finger placement guide 395, which is opposed to the first pinch face. The finger placement guide should help position the fingers on the gripping device properly and further aid in gripping the gripping device during use. Similarly, in one aspect, the second gripper member is equipped with a finger placement guide which is opposed to the second pinch face. In one aspect, the finger placement guides 395 consist of a raised area of sufficient height to prevent substantial movement of the fingers during normal use of the gripping device.

Another embodiment of the invention relates to a method of preventing movement of a urinary catheter 100 relative to a urinary catheter pouch by using the apparatuses as described herein.

In one aspect, the method comprises the steps of a) providing a urinary catheter that is at least partially disposed in the interior cavity of a urinary catheter pouch; and b) selectively pressing opposed gripper members toward each other to thereby force opposed portions of the gripper members to frictionally engage the urinary catheter with sufficient force to selectively prevent movement of the urinary catheter relative to the catheter pathway 330. Once the gripper members are engaged with the urinary catheter, the catheter 100 may be advance therethrough the port 210 in the urinary catheter pouch 200 for the user to perform necessary functions, such as, for example, insertion into the urethra.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims.

Moreover, although specific terms are employed herein, as well as in the claims which follow, they are used only in a generic and descriptive sense, and not for the purposes of limiting the described invention, nor the claims which follow.

What is claimed is:

1. A urinary catheter gripping device for use with a urinary catheter located within an interior cavity of a urinary catheter pouch, the catheter pouch having an exterior surface, a front face and a back face, the gripping device comprising:
   a gripper assembly comprising:
      a first gripper member comprising a first pinch face;
      a second gripper member comprising a second pinch face; wherein the first gripper member and the second gripper member are connected and define a catheter pathway; and
   a means for attaching the gripper assembly to the exterior surface of the urinary catheter pouch such that the catheter located within the interior cavity of the urinary catheter pouch is positioned substantially within the catheter pathway;
   wherein at least a portion of at least one of the first and second gripper members are selectively movable between a first, relaxed position, in which the respective first and second pinch faces of the first and second gripper members are spaced therefrom and do not engage the urinary catheter and the catheter is free to move relative to the catheter pathway, and a second position, in which at least a portion of the respective first and second pinch faces of the first and second gripper members engage a portion of the urinary catheter such that the catheter is prevented from moving relative to the catheter pathway.

2. The urinary catheter gripping device of claim 1, wherein the first pinch face of the first gripper member is positioned adjacent the second pinch face of the second gripper member.

3. The urinary catheter gripping device of claim 2, wherein the first pinch face of the first gripper member substantially faces the second pinch face of the second gripper member, and wherein the second pinch face of the second gripper member is configured to cooperate with the first pinch face of the first gripper member.

4. The urinary catheter gripping device of claim 1, wherein the first gripper member further comprises a first mount member that is hingedly connected to the first pinch face.

5. The urinary catheter gripping device of claim 4, wherein the second gripper member further comprises a second mount member that is connected to the second pinch face.

6. The urinary catheter gripping device of claim 5, wherein the second mount member is hingedly connected to the second pinch face.

7. The urinary catheter gripping device of claim 5, wherein the first mount member is connected to the second mount member.

8. The urinary catheter gripping device of claim 7, further comprising at least one male tab extending therefrom at least one of the respective first and second mount members that is configured to be operatively received within at least one female cavity defined therein at least one of the respective first and second mount members.

9. The urinary catheter gripping device of claim 8, wherein the at least one male tab and the at least one female cavity form a snap-fit connection.

10. The urinary catheter gripping device of claim 8, wherein the means for attaching the gripper assembly to a portion of the urinary catheter pouch comprises interposing the exterior surface of the urinary catheter pouch therebetween the connected first and second mount members; wherein the first mount member is connected to the front face of the urinary catheter pouch and the second mount member is connected to the back face of the urinary catheter pouch.

11. The urinary catheter gripping device of claim 1, wherein the first gripper member and the second gripper member are selectively and releasably connected to each other.

12. The urinary catheter gripping device of claim 1, wherein at least one of the respective first and second pinch faces comprises a plurality of triangular pincher points.

13. The urinary catheter gripping device of claim 1, wherein the first gripper member further comprises a finger placement guide formed thereon the first gripper member, and wherein the finger placement guide is opposed to the first pinch face of the first gripper member.

14. The urinary catheter gripping device of claim 13, wherein the second gripper member further comprises a finger placement guide formed thereon second gripper member, and wherein the finger placement guide is opposed to the second pinch face of the second gripper member.

15. The urinary catheter gripping device of claim 1, wherein the gripper assembly comprises a substantially rigid polymer.

16. A catheter package, comprising:
   a urinary catheter pouch having an exterior surface and defining a port in the exterior surface that is in communication with an interior cavity of the urinary catheter pouch;
   an elongate urinary catheter that is substantially disposed therein the urinary catheter pouch, wherein the urinary catheter is configured to selectively pass therethrough the port in the urinary catheter pouch;

a gripper assembly comprising:
  a first gripper member comprising a first pinch face;
  a second gripper member comprising a second pinch face; wherein the first gripper member and the second gripper member are connected to each other and define a catheter pathway; and
a means for attaching the gripper assembly to the exterior surface of the urinary catheter pouch such that the catheter located within the interior cavity of the urinary catheter pouch is positioned substantially within the catheter pathway;
wherein at least a portion of at least one of the first and second gripper members are selectively movable between a first, relaxed position, in which the respective first and second pinch faces of the first and second gripper members are spaced therefrom and do not engage the urinary catheter and the catheter is free to move relative to the catheter pathway, and a second position, in which at least a portion of the respective first and second pinch faces of the first and second gripper members engage a portion of the urinary catheter such that the catheter is prevented from moving relative to the catheter pathway.

17. The catheter package of claim 16, wherein the catheter is lubricated.

18. A method of advancing a urinary catheter relative to a urinary catheter pouch, comprising:

a) providing a urinary catheter that is at least partially disposed therein an interior cavity of the urinary catheter pouch;
b) selectively pressing opposed gripper members, which are mounted to opposed portions of an exterior surface of the urinary catheter pouch and that are configured to form a catheter pathway that partially surrounds a portion of the urinary catheter that is disposed therein the interior cavity of the urinary catheter pouch, toward each other, from an open, relaxed and spaced position, to thereby force opposed portions of the urinary catheter pouch to frictionally engage the urinary catheter with sufficient force to selectively prevent movement of the urinary catheter relative to the catheter pathway;
c) advancing a portion of the urinary catheter therethrough a port therein a portion of the urinary catheter pouch while maintaining the engagement between the engaged portion of the urinary catheter pouch and the urinary catheter;
d) releasing the opposed gripper members to enable them to return to the open and relaxed state, thereby allowing movement of the urinary catheter pouch, along with the gripper members, relative to the urinary catheter to reposition the gripper members along the urinary catheter; and
e) repeating steps (c) and (d) until the urinary catheter is positioned in a desired location.

\* \* \* \* \*